United States Patent [19]

Nardella

[11] Patent Number: 5,293,868
[45] Date of Patent: Mar. 15, 1994

[54] CARDIAC ABLATION CATHETER HAVING RESISTIVE MAPPING ELECTRODES

[75] Inventor: Paul C. Nardella, North Easton, Mass.

[73] Assignee: American Cardiac Ablation Co., Inc., Taunton, Mass.

[21] Appl. No.: 906,819

[22] Filed: Jun. 30, 1992

[51] Int. Cl.⁵ .............................. A61B 5/04
[52] U.S. Cl. .................... 128/642; 607/154; 607/119; 606/46
[58] Field of Search ............ 128/642, 783–786, 128/804, 395–398; 606/32, 33, 41, 46, 48, 45, 49; 607/115, 116, 154, 119

[56] References Cited

U.S. PATENT DOCUMENTS

| | | | |
|---|---|---|---|
| 4,641,649 | 2/1987 | Walinsky et al. | 128/786 |
| 4,754,757 | 7/1988 | Feucht | 606/32 |
| 4,762,136 | 8/1988 | Baker, Jr. | 128/786 |
| 4,785,815 | 11/1988 | Cohen | 128/642 |
| 4,832,048 | 5/1989 | Cohen | 128/786 |
| 4,869,248 | 9/1989 | Narula | 128/642 |
| 4,892,102 | 1/1990 | Astrinsky | 128/642 |
| 4,896,671 | 1/1990 | Cunningham et al. | 128/642 |
| 4,940,064 | 7/1990 | Desai | 128/784 |
| 4,945,912 | 8/1990 | Langberg | 128/642 |
| 4,966,597 | 10/1990 | Cosman | 128/736 |
| 4,976,711 | 12/1990 | Parins et al. | 606/48 |
| 5,005,180 | 4/1991 | Edelman et al. | 128/397 |
| 5,156,151 | 10/1992 | Imran | 128/642 |

Primary Examiner—Stephen C. Pellegrino
Assistant Examiner—M. Peffley
Attorney, Agent, or Firm—Lahive & Cockfield

[57] ABSTRACT

A cardiac ablation catheter includes a distal, energy delivering electrode and at least one sensing electrode proximal to the energy delivering electrode. The catheter communicates with an electrosurgical generator which provides electrical energy, such as a radio frequency energy, to the distal electrode. The sensing electrodes communicate with a monitor for recording electrical signals within the heart. One or more resistors is positioned adjacent each sensing electrode, and in series with a conductor associated with the sensing electrode, to reduce or eliminate any current tending to be emitted through the sensing electrodes as a result of delivery of electrical current through the distal electrode.

8 Claims, 1 Drawing Sheet

CARDIAC ABLATION CATHETER HAVING RESISTIVE MAPPING ELECTRODES

BACKGROUND OF THE INVENTION

This invention relates to intravascular catheters, and more particularly to endocardial ablation catheters and to their method of use in treating arrhythmia using radio frequency energy.

The heart is a muscular organ comprising four separate chambers which cooperate to pump blood throughout the body. The heart muscles must contract and relax in a coordinated sequence in order for blood to be passed through the circulatory system in an efficient manner. The heart includes a specialized system for generating impulses to cause rhythmical contraction of the heart muscle and for conducting these impulses rapidly through the heart. In the proper sequence the atria contract about one sixth of a second prior to ventricles. This enables extra filling of the ventricles before they contract to pump blood through the lungs and to other areas of the body.

The rhythmic impulse of the heart is generated in the sinoatrial node (SA node). The SA node has an inherent rhythm which can be modified by the sympathetic and parasympathetic nervous system. The impulse initiated by the SA node spreads through the atrium to the atrio-ventricular node (AV node), and then through the Purkinje fibers to the endocardial surfaces of the ventricles.

The rhythmical and conduction system of the heart is susceptible to disruption by disease. Such damage can result from the inability of the cardiac conduction pathways to properly transmit the electrical impulses generated in the SA node, leading to arrhythmias, or irregular heartbeats. Cardiac arrhythmias can often be detected through electrocardiograms.

Some forms of cardiac arrhythmia are able to be controlled through medication. However, other forms of arrhythmia do not respond to medication. Moreover, medication typically does not remedy the problem, and the dosage and the medication type must be changed periodically for continued control of the problem.

One alternative to medication is the surgical removal of a portion of the cardiac pathway which is responsible for the arrhythmia. The many dangers associated with open heart surgery render this a less preferred treatment option. Recently, however, it has become possible to intravascularly insert a specialized catheter within the heart, for positioning adjacent to the conduction tissue responsible for the arrhythmia. The catheter is adapted to deliver energy (e.g., radio frequency energy) to ablate or destroy the tissue from which the arrhythmia emanates. This has been found to be a relatively safe and effective technique for eliminating many forms of arrhythmia. Various ablation catheters and techniques for their use are described in U.S. Pat. Nos. 4,641,649; 4,785,815; 4,869,248; and 4,896,671.

Cardiac ablation catheters typically have at least one electrode at the distal end of the catheter which is adapted to deliver energy to the affected tissue. Other electrodes can be proximally positioned on the catheter and used for sensing endocardial signals. Ablation may be achieved by the application of electrical energy, such as radio frequency (RF) or direct current (DC) energy, from a generator source, through a conductor disposed within the catheter, and to the distal electrode.

During an ablation procedure it is essential to locate the distal, energy delivering electrode precisely at the site or sites of the arrhythmia. The proximal sensing electrodes aid in the proper positioning of the distal electrode. However, the sensing electrodes of the catheter often are in close proximity to the distal electrode, and to healthy cardiac tissue as well. The ablating energy usually travels through a conductor within the body of the catheter parallel and in close proximity to conductors attached to the sensing electrodes. Due to the need for minimal cross-sectional width and maximum flexibility of the catheter, the amount of insulating material which can encase each conduct is limited. Capacitive and/or inductive coupling can thus occur between these conductors when energy is supplied to the distal electrode. This capacitive effect can direct an unwanted amount of electrical current into the sensing electrodes. The delivery of this current, even in low levels, is potentially damaging to otherwise healthy tissue adjacent to the sensing electrodes. Moreover, the unwanted delivery of energy through the proximal electrodes reduces the amount of ablating energy which could otherwise be delivered through the distal electrode.

Accordingly, it is desirable to provide a catheter construction which minimizes the potential for delivery of energy through sensing electrodes used with an ablation catheter, and which maximizes the amount of energy delivered for an ablation procedure.

It is thus an object of the invention to provide an ablation catheter construction which minimizes the potential for inadvertently damaging healthy tissue during a cardiac ablation procedure. Another object is to Provide an ablation catheter which maximizes the amount of energy delivered through the distal electrode. Other objects will be apparent upon review of the disclosure which follows.

SUMMARY OF THE INVENTION

Capacitive and/or inductive coupling can often cause current delivered to a distal ablating electrode through a conductor wire also to be delivered to sensing electrode(s) through conductor wires in close proximity to the conductor which delivers ablating energy. Capacitive or inductive coupling also lowers the amount of current available for delivery through the distal electrode to an ablation site.

The invention is directed to an endocardial ablation catheter having at least one electrode for delivering ablating energy to cardiac tissue, at least one electrode for sensing endocardial signals, and at least one element which limits the effects of capacitive (or inductive) coupling, such as a resistor or inductor, connected between each sensing electrode and each associated conductor. The element preferably is placed in close proximity to the sensing electrode and minimizes the unwanted delivery of electrical current through the sensing electrode during delivery of ablation energy through the ablating electrode. The placement of the element in Proximity to the sensing electrode also renders the conductor leading to the distal electrode the path of lowest impedance and thus facilitates the delivery of a greater percentage of available energy through the distal electrode. Ablation catheters which require multiple sensor electrodes have one or more resistors between each sensor electrode and its associated conductor.

The catheter construction of the present invention is particularly well suited for use in cardiac ablation procedures. However, the catheter is also suitable for use in procedures affecting other organs and tissues where damage to healthy tissue adjacent a target area is to be avoided.

BRIEF DESCRIPTION OF THE DRAWINGS

Other features, objects and benefits of the invention can be more clearly understood with reference to the following description of an illustrative embodiment, and to the drawings, in which.

DETAILED DESCRIPTION OF THE INVENTION

Figure 1:
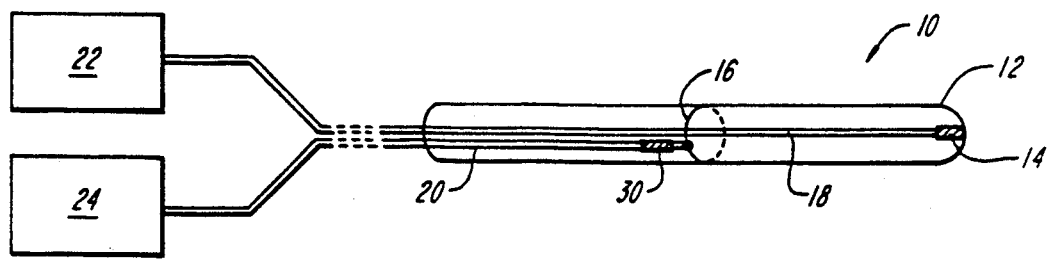
FIG. 1 is a schematic representation of a cardiac ablation catheter system according to the present invention.

FIG. 1 illustrates an ablation catheter 10 adapted to access a body through a vessel for deployment within or adjacent to internal organs or tissue. The catheter is particularly well adapted for use in ablating endocardial tissue which contributes to arrhythmias. However, the catheter may be used for procedures affecting other organs and tissues as well. The catheter 10 has an outer wall 12 having disposed thereon a distal ablation electrode 14 and at least one proximal, annularly-disposed sensing electrode 16. The distal ablation electrode 14 is electrically connected to an electrosurgical energy source 22 through conductor 18. Similarly, sensing electrode 16 is electrically connected through electrical conductor 20 to a device 24 for monitoring endocardial signals. [VERIFY] A resistor 30 is located in series with conductor 20 and preferably is positioned in close proximity to the sensing electrode 16.

Figure 2:
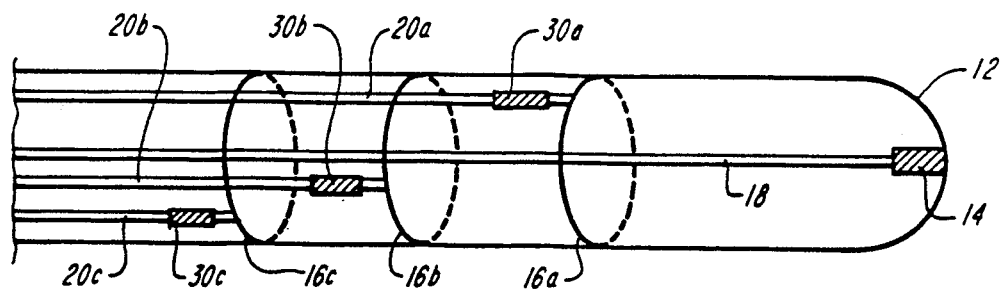
FIG. 2 is a schematic representation of a portion of a cardiac ablation catheter constructed according to the present invention.

FIG. 2 illustrates another embodiment of the invention in which catheter 10 features three annular sensing electrodes 16a, 16b, 16c, all of which are positioned proximally to the distal electrode 14. Each sensing electrode is connected to a monitoring device (not shown) through its respective conductor 20a, 20b, 20c. Also, a resistor (or inductor) 30a, 30b, 30c is positioned at the terminal end of each conductor, in close proximity to each sensing electrode 16a, 16b, 16c.

As noted above, the proximity of distal electrode conductors 18 to sensing electrode conductors 20 can result in capacitive or inductive coupling during delivery of ablation energy through conductor 18. This, in turn, can result in the unwanted delivery of some current through the sensing electrodes. A further disadvantage of capacitive or inductive coupling is that a portion of the current intended for delivery through the distal electrode is instead delivered through the proximal electrodes. This can have an adverse effect on an ablation procedure since the amount of current delivered to the ablation site can be less than what is intended or desired. The placement of resistors (or inductors) 30a, 30b, 30c in series with sensing electrode conductors 20a, 20b, 20c prevents or minimizes unintentional leakage of Potentially harmful or undesirable amounts of current though sensing electrodes 16a, 16b, 16c.

The ablation catheter 10 can be of any type typically used for cardiac ablation procedures. Exemplary catheter constructions are disclosed in U.S. Pat. Nos. 4,641,649; 4,869,248; and 4,896,671, each of which is incorporated by reference herein. Generally, the catheter is a thin, flexible, elongate member having dimensions which make it suitable for intravascular delivery to the heart or to other organs. The diameter of the catheter varies depending upon its desired use, however, the diameter is typically in the range of about 4 to 12 French (0.052 inch to 0.156 inch). Most preferably the catheter diameter is in the range of about 4 to 7 French (0.052 to 0.091 inch).

The distal electrode 14 preferably is one which is able to deliver electrosurgical ablation energy to cardiac tissue. Preferably, radio frequency energy, at about 100 KHz to 2 mHz, and preferably at about 500 to 750 kHz is delivered through the electrode 14. The distal electrode 14 typically is approximately 2 to 6 mm in length and about 24 to 42 $mm^2$ in surface area. In one preferred embodiment the electrode is about 4 mm in length and about 27 $mm^2$ in surface area.

The sensing electrodes 16 may be annularly disposed on the surface 12 of the catheter 10. Although the sensing electrodes typically are ring-shaped, these electrodes may assume other shapes and orientations which are well known in the art.

The sensing and distal electrodes can be made of a variety of suitable materials which are well known for use with ablation catheters and other electrosurgical devices. General requirements of such materials are that they be good electrical conductors, and that they be inert materials with good biocompatibility. Examples of suitable materials include stainless steel, gold, silver, platinum, and silver-silver chloride.

Conductors 18, 20 useful with the present catheter construction are those which typically are insulated conductors of the type used in the design of endocardial catheters which deliver electrosurgical (e.g., radio frequency) energy to tissue. The conductors preferably are flexible and are of a diameter suitable to fit within the catheter body. The actual diameter of the conductors can vary because the diameter of the catheter body can vary.

The electrosurgical generator 22 useful with the catheter should be capable of delivering radio frequency energy at a range of about 100 kHz to 2 mHz and preferably at about 500 to 750 kHz. The power delivered is about 20 to 40 W, and most preferably about 30 watts. Typically, ablation procedures deliver from 15 to 100 volts, and more preferably from about 45 to 60 volts, between the distal electrode and an electrosurgical ground pad typically mounted on the chest wall of the patient. The generator should be used in conjunction with a device (not shown) which provides real-time monitoring of rms voltage, current and impedance.

Resistors suitable for use with the present catheter 10 include those which are of suitable dimensions to fit within the catheter body. Moreover, the resistors 20 must be configured for minimal physical and electromagnetic interference with other conductors, and minimal inductance between conductor 18 and resistors 30. The resistors 30 may be selected from among several types, including thin-film, ceramic, wire wound, and highly resistive wire such as tungsten and nickel-chromium. One skilled in the art can readily determine the appropriate resistor type and resistor value for use with a given ablation catheter. As noted, one or more resistors preferably are placed adjacent to and in close proximity to electrodes 16. The resistance is preferably concentrated close to the electrode to Prevent spreading the resistance over the length of the conductor 20 which communicates with electrodes 16. Although it is less preferred, resistors 30 may be inserted in series along the length of the conductor 20.

Preferably, the resistors have a nominal value of about 500 to 1300 ohms, and most preferably 1000 ohms.

The inductors suitable for use with the invention include wire coil and ferrite core bead inductors as well as others known in the art which Possess suitable resistance at the operating frequency of the ablation catheter.

During a cardiac ablation procedure, energy, typically in the form of radio frequency energy, is generated and delivered to an ablating electrode 14 through one or more conductors disposed in the catheter. The energy is then communicated from the electrode to adjacent tissue and eventually to a remote ground electrode (not shown). During energy delivery, the effect of any capacitive coupling is minimized or eliminated by resistors 30. That is, the resistors reduce or eliminate the density of any electrical current tending to inadvertently exit sensing electrodes 16. To the extent that any current does exit sensing electrodes 16, the current is of non-therapeutic intensity so that it has no detrimental effect on tissue disposed adjacent the sensing electrodes 16. A further function of the resistors 30 is that they prevent a drain on current available for release through distal electrode 14, and thus make more current available for delivery during the ablation procedure.

Although the invention has been described with respect to a cardiac ablation catheter, it is understood that the invention is applicable to all catheters which include sensing electrodes in proximity to an energy delivering electrode. Further, various modifications may be made to the invention described herein without departing from the intended scope of the invention.

What is claimed is:

1. A catheter device for deployment within or adjacent to an internal organ, comprising:

a thin, elongate, flexible member having distal and proximal ends;

an energy delivering ablation electrode positioned on the member;

an electrical conductor for communicating ablating energy from a generator source to the energy delivering ablation electrode;

at least one sensing electrode disposed on the member;

an electrical conductor communicating with each sensing electrode; and resistor means for reducing the density of electrical current exiting each sensing electrode upon delivery of ablating energy through the ablation electrode to adjacent tissue, the resistor means being disposed adjacent to each sensing electrode at a terminal end of the electrical conductor associated with each sensing electrode.

2. The device of claim 1, wherein said means for reducing the density of electrical current is electrically connected in series with the sensing electrodes and the associated electrical conductors.

3. The device of claim 2, wherein the means for reducing the density of electrical current has nominal resistive values of about 500 to 1300 ohms.

4. The device of claim 3, wherein the means for reducing the density of electrical current is selected from the group consisting of thin-film, wire-wound, resistive wire and ceramic resistors.

5. The device of claim 1 wherein the means for reducing the density of electrical current is an inductor.

6. The device of claim 1, wherein the catheter is a cardiac ablation catheter.

7. The device of claim 1 wherein the energy delivering electrode is mounted on the distal end of the member.

8. The device of claim 6 wherein the sensing electrode is disposed proximally to the energy delivering electrode.

* * * * *